(12) United States Patent
Zhao et al.

(10) Patent No.: US 8,964,019 B2
(45) Date of Patent: Feb. 24, 2015

(54) ARTIFICIAL COMPOUND EYE WITH ADAPTIVE MICROLENSES

(75) Inventors: Yi Zhao, Columbus, OH (US); Hansong Zeng, Columbus, OH (US)

(73) Assignee: The Ohio State University, Columbus, OH (US)

( * ) Notice: Subject to any disclaimer, the term of this patent is extended or adjusted under 35 U.S.C. 154(b) by 562 days.

(21) Appl. No.: 13/336,075

(22) Filed: Dec. 23, 2011

(65) Prior Publication Data

US 2013/0162788 A1  Jun. 27, 2013

(51) Int. Cl.
 *A61B 3/113* (2006.01)
(52) U.S. Cl.
 USPC .......................................................... 348/78
(58) Field of Classification Search
 None
 See application file for complete search history.

(56) References Cited

U.S. PATENT DOCUMENTS

| 7,672,058 | B2 | 3/2010 | Jiang et al. | |
|---|---|---|---|---|
| 2008/0249469 | A1* | 10/2008 | Selvaganapathy et al. | ... 604/151 |
| 2009/0314929 | A1* | 12/2009 | Lee et al. | ................. 250/227.28 |

* cited by examiner

*Primary Examiner* — William C Vaughn, Jr.
*Assistant Examiner* — Eileen Adams
(74) *Attorney, Agent, or Firm* — Jason H. Foster; Kremblas & Foster

(57) ABSTRACT

An artificial compound eye formed of three layers of membrane bonded to one another in a stacked relationship. A field chamber is located intermediate the two bottommost membranes. A plurality of focus chambers is located intermediate the two topmost membranes, and an image sensor is located below each focus chamber. The field chamber and each focus chamber contain a pressurized fluid medium. The ceilings of the focus chambers function as lenses though which light must pass to reach the sensors. The fluid pressure in the field chamber can be varied to expand or contract the eye between a planer and a domed configuration, thereby allowing the field of view of the eye to be varied. The fluid pressure in each focus chamber can be varied to expand or contract each lens between a planar and a domed configuration for independently varying the focal length of each lens.

29 Claims, 5 Drawing Sheets

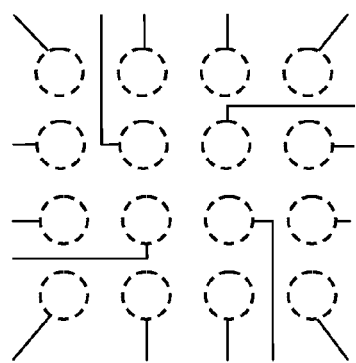
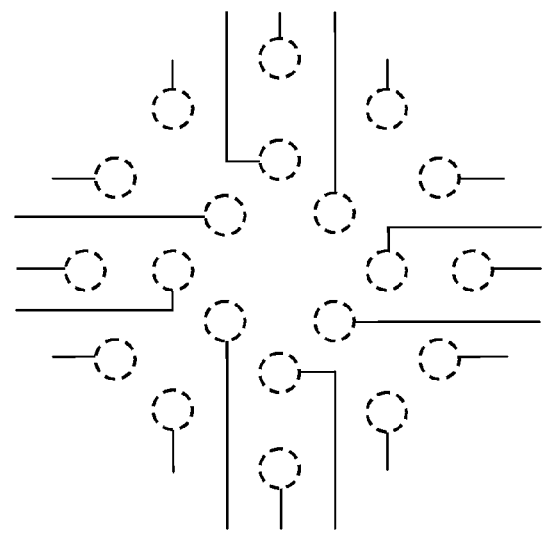
Fig. 6　　　　　　　　Fig. 7
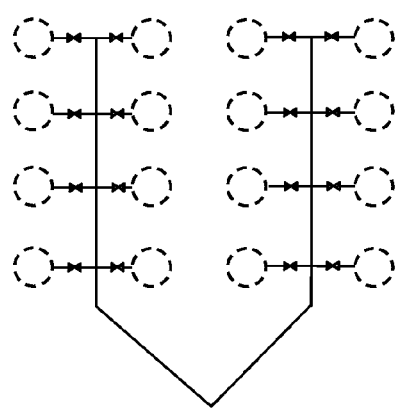
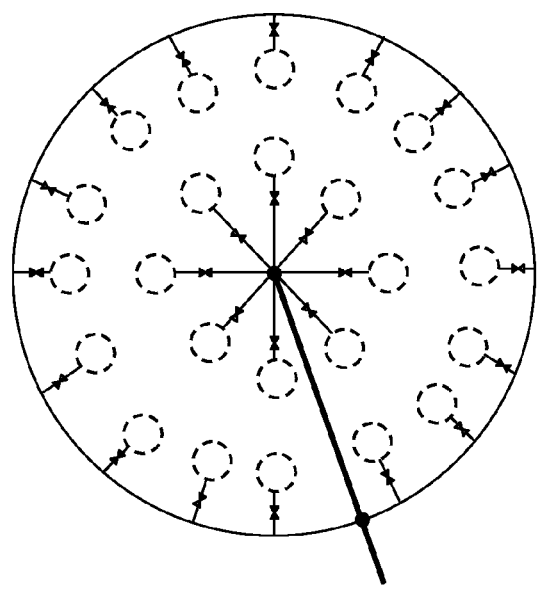
Fig. 8　　　　　　　　Fig. 9

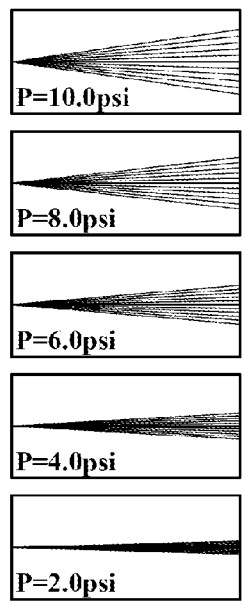
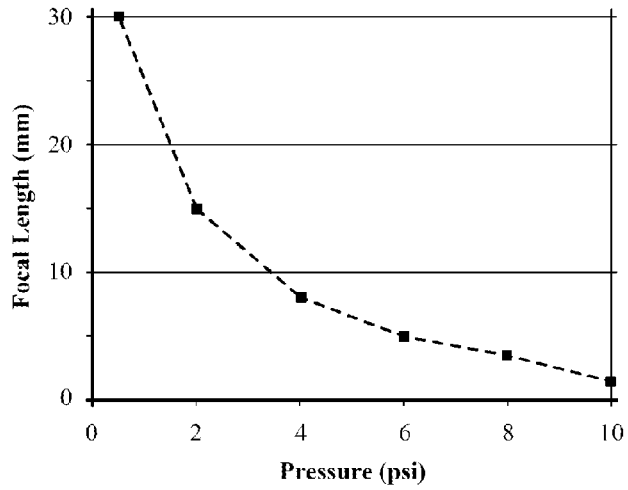
Fig. 14
Fig. 15
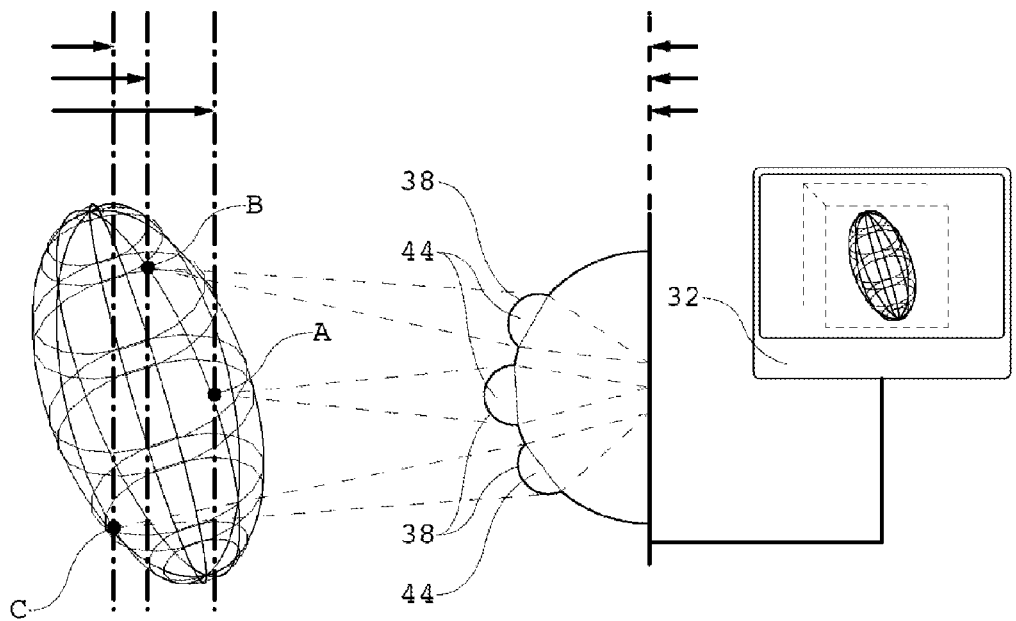
Fig. 16

ARTIFICIAL COMPOUND EYE WITH ADAPTIVE MICROLENSES

BACKGROUND OF THE INVENTION

Optical lenses have become ubiquitous over the past several decades and are now used in a wide range of applications in a variety of fields, including consumer products (e.g. cameras, camcorders, cellular telephones, telescopes, etc), civilian and military surveillance, optical microsurgery, and endoscopic visualization. A conventional optical lens is typically made of transparent material and has a concave or convex shape that is tailored to suit a specific application. Particularly, a conventional lens is designed with a "focal length" that is generally determined by the curvature of the lens. "Focal length" is the distance over which initially colineated rays of light passing through a lens are brought to a focus (i.e. converged).

Shortcomings of conventional optical lenses include that the focal length of such a lens is fixed after fabrication. Focusing on objects that are positioned at varying distances from the lens therefore requires physical movement of the lens toward and away from the objects. Furthermore, the field-of-view of the lens is limited and is coupled to the focal length. That is, it is difficult to simultaneously obtain a long working distance and a wide field-of-view. Still further, a single lens component can only focus on a single viewing field at a certain distance from the lens at a given time. As a result, the lens cannot be used to acquire three-dimensional imaging with depth perception in real-time.

Looking to the natural world, one can find examples of optical lenses that overcome some of the limitations discussed above incorporated into the physiology of various animals. For example, predatory mammalian animals typically have a pair of forward-looking camera eyes, each having a single lens with an adaptively adjustable focal length for obtaining a clear image of objects at various distances. Numerous ocular nerves in the eyes of such animals provide relatively high definition images. However, due to their position and orientation, mammalian camera eyes cannot provide a wide field-of-view.

In contrast to the camera eyes of mammals, flying insects have compound eyes that are composed of hundreds, and in some cases thousands or millions, of small eyes (ommatidia) that are arranged on a generally spherical underlying structure. In these species, each small eye (ommatidium) has a fixed focal length and is responsible for providing a view of a certain field ahead of it. A single nerve corresponds to each ommatidium and delivers one pixel to the vision process center in the brain of the insect where a complete, unified image is created. Compared to a camera eye, the compound eye usually has poor resolution, which is generally attributable to the poor image processing capability of an insect's small brain. However, because of the spherical configuration of the compound eye and the resulting orientations of the numerous ommatidia distributed thereon, the eye provides a much wider field-of-view compared to a camera eye.

The need exists for an optical lens system that overcomes the disadvantages of the prior art and would be suitable for a variety of commercial and non-commercial applications. Specifically, it would be advantageous to provide an optical lens system that features a wide field of view, variably adjustable focal length, high definition images, and is relatively small in size and inexpensive to produce.

BRIEF SUMMARY OF THE INVENTION

In accordance with the present invention, there is provided an artificial compound eye having a plurality of independently-focusable micro-lenses. The eye is formed of three layers of silicone membrane that are covalently bonded to one another in a stacked, flatly-abutting relationship. The bottom layer of membrane, hereinafter referred to as the substrate membrane, has a circular depression formed in its top surface. A narrow groove is also formed in the top surface of the substrate membrane and intersects and extends away from the circular depression to a fluid inlet that is preferably located adjacent an edge of the membrane.

The middle layer of membrane, hereinafter referred to as the intermediate membrane, is sealed over both the circular depression and the narrow groove in the top surface of the substrate membrane, thus forming an enclosed, circular fluid chamber, hereinafter referred to as the field chamber, and a microfluidic channel that is in fluid communication with the field chamber. The field chamber and the microfluidic channel contain a fluid medium that is generally kept under pressure by a microfluidic pump that is operatively connected to the fluid inlet.

A flexible circuit having a plurality of image sensors arranged in a predefined pattern is embedded in the top surface of the intermediate membrane in a substantially parallel relationship therewith. Image data that is captured by the image sensors is transmitted to a central processing unit, preferably by wireless communication means, where the data is used to generate and display a single, cohesive image that represents the total field of view of all of the image sensors.

The top layer of membrane, hereinafter referred to as the outer membrane, has a plurality of circular depressions formed in its bottom surface in a configuration that is substantially identical to the configuration of the image sensors in the intermediate layer. A plurality of narrow grooves is also formed in the bottom surface of the outer membrane with each groove intersecting and extending away from one of the circular depressions to a fluid inlet that is preferably located adjacent an edge of the membrane. The outer membrane is sealed over the image sensors with each circular depression in the outer membrane aligned with an image sensor in the intermediate membrane, thereby forming a circular fluid chamber, hereinafter referred to as a focus chamber, between each image sensor and the outer membrane. The recessed areas of the outer membrane that form the ceilings of the focus chambers thereby form lenses through which light must pass to reach the image sensors.

Each narrow groove in the bottom surface of the outer membrane forms a microfluidic channel that is in fluid communication with a corresponding focus chamber. The focus chambers and the microfluidic channels contain a refractive fluid medium that is generally kept under pressure by a plurality of microfluidic pumps that are each operatively connected to the fluid inlet of a channel.

During operation of the eye, a user can manipulate the microfluidic pump that is connected to the field chamber to increase or decrease the amount of fluid pressure within the chamber, thereby causing the eye to expand or contract between a substantially planar configuration and a convex, domed configuration. When the eye is in a planar configuration, the lenses in the outer membrane and the image sensors in the intermediate membrane are oriented in a generally parallel, forward-looking configuration. When the eye is expanded, the convexity of the eye increases and the lenses and image sensors are moved into an offset, omni-directional configuration. Thus, by varying the fluid pressure in the field chamber, the overall field of view of the eye can be increased or decreased.

Similarly, a user can manipulate the microfluidic pumps that are connected to the focus chambers to increase or decrease the amount of fluid pressure within each chamber, thereby causing the flexible lenses to expand or contract between a substantially planar configuration and a convex, domed configuration. Thus, by varying the fluid pressure in each focus chamber, the focal length of each lens can be varied for allowing each image sensor to independently focus on objects that are positioned at varying distances from the eye.

The above-described eye structure therefore allows the field of view of the eye to be tuned independently of the focal length of any of the eye's lenses. Moreover, because the image sensors of the eye are always oriented perpendicular relative to the axis of the lenses, the eye facilitates a wide field of view without the image distortion that is associated with traditional wide angle lenses. The eye therefore provides the advantages of both camera eyes and compound eyes without the disadvantages associated with either.

BRIEF DESCRIPTION OF THE SEVERAL VIEWS OF THE DRAWINGS

FIG. 6 is a top view illustrating a first alternative configuration of the focus chambers and microfluidic channels of the eye.

FIG. 7 is a top view illustrating a second alternative configuration of the focus chambers and microfluidic channels of the eye.

FIG. 8 is a top view illustrating a third alternative configuration of the focus chambers and microfluidic channels of the eye that incorporates valves.

FIG. 9 is a top view illustrating a fourth alternative configuration of the focus chambers and microfluidic channels of the eye that incorporates valves.

FIG. 14 is a chart illustrating the convergence of light passing through a lens of the eye when expanded by various fluid pressures.

FIG. 15 is a graph illustrating a relationship of the focal length of a lens of the eye and fluid pressure that is applied to the lens.

FIG. 16 is a schematic view illustrating the use of the eye as a means for facilitating real-time, 3D imaging.

Figure 1:
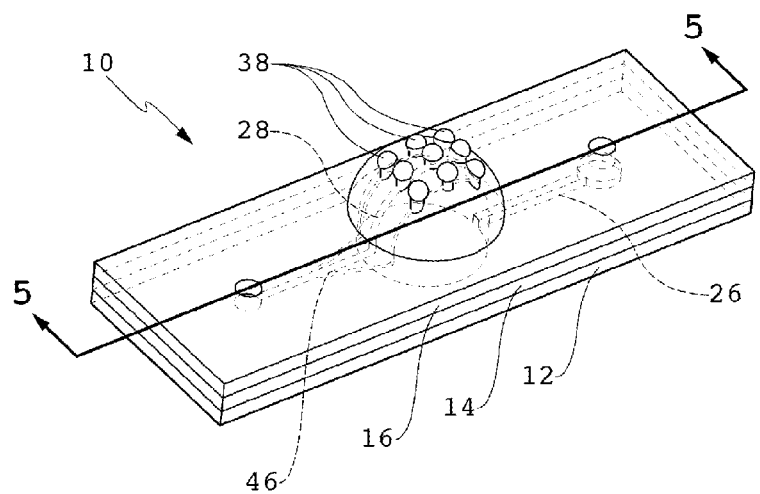
FIG. 1 is a perspective view illustrating a preferred embodiment of the present invention.

In describing the preferred embodiment of the invention which is illustrated in the drawings, specific terminology will be resorted to for the sake of clarity. However, it is not intended that the invention be limited to the specific term so selected and it is to be understood that each specific term includes all technical equivalents which operate in a similar manner to accomplish a similar purpose.

DETAILED DESCRIPTION OF THE INVENTION

Referring to FIG. 1, an artificial compound eye with adaptive microlenses (hereinafter referred to as "the eye") is indicated generally at 10. The eye 10 generally includes a substrate membrane 12, an intermediate membrane 14 bonded to the substrate membrane 12, and an outer membrane 16 bonded to the intermediate membrane. For the sake of convenience and clarity, terms such as "top," "bottom," "up," "down," "inwardly," and "outwardly" will be used herein to describe the relative placement and orientation of various components of the eye 10, all with respect to the geometry and orientation of the eye 10 as it appears in FIG. 1.

Figure 2:
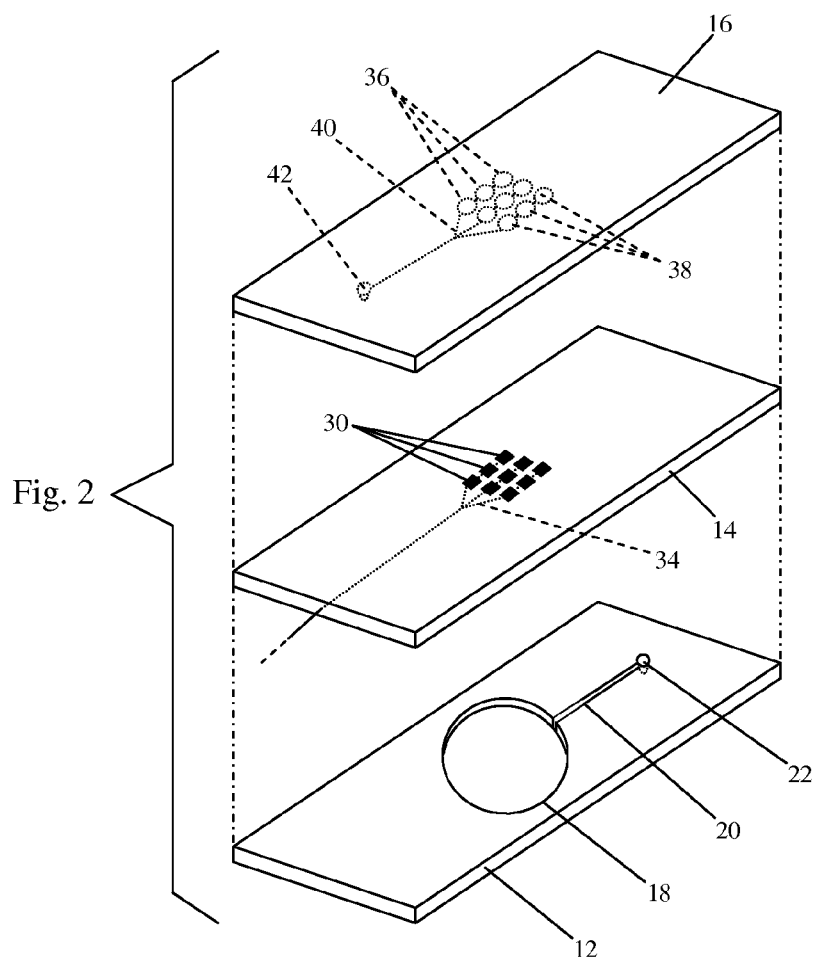
FIG. 2 is an exploded view illustrating the preferred embodiment of the present invention shown in FIG. 1.

Referring to FIG. 2, the substrate membrane 12 is preferably formed of silicone polymer and has an overall thickness of 1000 µm. It is contemplated that substrate membrane 12 can alternatively be formed of any other suitable material, such as glass, plastic, metal, or elastic or resilient polymer, and that the thickness of the substrate membrane 12 can be varied to suit a particular application without departing from the present invention. During fabrication, the substrate membrane 12 is preferably subjected to an etching or casting process whereby a circular depression 18 is formed in the top surface of the substrate membrane 12. The circular depression 18 is 100 µm deep and has a diameter of 10 mm, although it is contemplated that the dimensions of the depression 18 can be varied. It is further contemplated that the depression 18 can have a shape other than circular, such as oval, rectangular, triangular, or irregular.

A narrow groove 20 that is preferably shallower than the circular depression 18 is also formed in the top surface of the substrate membrane 12 using an etching or casting process. The groove 20 intersects and extends away from the circular depression 18 to a fluid inlet 22 that is preferably located intermediate the circular depression 18 and an edge of the substrate membrane 12, although the particular location of the fluid inlet 22 is not critical. While an etching or casting process is preferred for forming the circular depression 18 and the groove 20 in the substrate membrane 12, it is contemplated that any other suitable method, including, but not limited to, soft lithography, injection molding, hot embossing, and other cutting, molding, or casting methods, can additionally or alternatively be employed.

Still referring to FIG. 2, the intermediate membrane 14 is formed of a layer of polydimethylsiloxane (PDMS) or other suitable material, such as polyurethane, clear acrylic, or parylene. The intermediate membrane 14 has a preferred thickness of 50 µm, although it is contemplated that the thickness of the membrane 14 can be varied. The intermediate membrane 14 has a substantially flat, featureless bottom surface that is adhered to the top surface of the substrate membrane 12 in a flatly abutting relationship therewith. The two parts 12 and 14 are preferably bonded to one another using a conventional covalent bonding process that will be familiar to those of ordinary skill in the art. With the flat bottom surface of the intermediate membrane 14 bonded to the top surface of the substrate membrane 12 thusly, the circular depression 18 in the substrate membrane 12 (described above) forms an enclosed, circular fluid chamber 24 (see FIGS. 3-5), hereinafter referred to as the "field chamber 24" (so-called for reasons that will become apparent below), between the membranes 12 and 14, wherein the intermediate membrane 14 forms a ceiling of the field chamber 24. Similarly, the groove 20 in the substrate 12 (discussed above) forms an enclosed, microfluidic channel 26 (see FIG. 1) between the parts 12 and 14 that is in fluid communication with the field chamber 24.

The field chamber 24 and the microfluidic channel 26 contain a fluid medium that is kept under pressure by a computer controlled, microfluidic pump (not shown) that is operatively connected to the fluid inlet 22. The fluid medium is preferably mineral oil having a refractive index n=1.4, although it is contemplated that any other liquid medium having a suitable refractive index and viscosity can alternatively be used. It is further contemplated that the fluid medium can alternatively be a pressurized gas. The purpose and operation of the field chamber 24 and the pressurized fluid medium will be described in greater detail below.

An alternative embodiment of the eye 10 is contemplated in which the circular field chamber 24 and the microfluidic channel 26 are defined by forming a circular depression and a groove in the bottom surface of the intermediate membrane 14 instead of in the top surface of the substrate membrane 12. In such an embodiment, the top surface of the substrate membrane 12 would be substantially flat and featureless for sealing over the circular depression and the groove in the intermediate membrane 14.

Referring to FIGS. 1 and 3-5, a flexible circuit 28 comprising an array of interconnected image sensors 30 is embedded in the intermediate membrane 14 in a substantially coplanar relationship therewith. The image sensors 30 are preferably CMOS or CCD sensors connected by flexible electrical wires, although it is contemplated that various other types of sensors can alternatively be used, including, but not limited to silicon transistors and polythiophene/fullerene sensors. The top surfaces of the sensors 30 (i.e. the surfaces of the sensors 30 that capture images) are preferably coplanar with, and are therefore not covered by, the top surface of the intermediate membrane 14. It is contemplated that the top surfaces of the sensors 30 can alternatively be recessed from the top surface of the intermediate membrane 14 and, positioned thusly, can optionally be covered by a thin, top layer of the intermediate membrane 14 if the membrane is sufficiently transparent.

Figure 10:
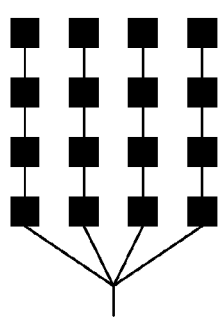
FIG. 10 is a top view illustrating a first alternative embodiment of the flexible circuit of the eye.
Figure 11:
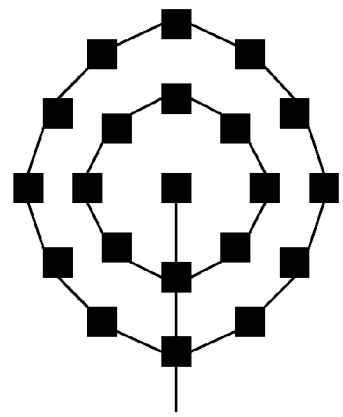
FIG. 11 is a top view illustrating a second alternative embodiment of the flexible circuit of the eye.

The exemplary embodiment of the eye shown in FIG. 1 incorporates a total of nine image sensors 30 arranged in a square, 3×3 configuration. However, it is contemplated that the number and configuration of the sensors 30 can be varied without departing from the invention. For example, referring to FIGS. 10 and 11, the eye 10 can alternatively include 16 image sensors in a square configuration or 21 image sensors in a concentric, circular configuration. Various other sensor configurations, such as triangular, oval, and irregular configurations, are also contemplated.

The image sensors 30 are operatively connected to a central processing unit (CPU), such as the general purpose computer 32 shown in FIG. 16, by conductors, such as a series of wires 34 that are embedded in, and extend through, the intermediate membrane 14. The wires 34 transmit image data from the image sensors 30 to the CPU 32 to be processed and displayed (described in greater detail below). Alternatively, it is contemplated that the image data can be transmitted wirelessly between the image sensors 30 and the CPU 32, such as through a Bluetooth transmitter or other wireless data communication means that is integrated into the flexible circuit 28. It is further contemplated that the image sensors 30 can communicate the image data to an external wireless communication means through a wired connection, and that the wireless communication means can then wirelessly transmit the image data to a CPU at a remote location.

Upon being received by the CPU 32, the image data captured by the several image sensors 30 in the sensor array are digitally "stitched together" using conventional software algorithms that are well known to those of ordinary skill in the art. The resulting output is a contiguous, preferably seamless image that is presented to a viewer, such as on a conventional computer monitor.

Referring again to FIG. 2, the outer membrane 16 is formed of a layer of PDMS or other suitable material, such as those discussed above in the description of the substrate membrane 12. The outer membrane 16 is 500 μm thick, although it is contemplated that the thickness of the membrane 16 can be varied. Like the substrate membrane 12 described above, the outer membrane 16 is subjected to an etching or casting process during fabrication whereby an array of circular depressions 36 is formed in the bottom surface of the membrane 16. Each circular depression 36 defines a relatively thin, circular lens 38 in the transparent outer membrane 16. Each depression 36 is 450 μm deep and has a diameter of 1.5 mm, although it is contemplated that the dimensions of the depressions 36 can be varied depending on the desired size and thickness of the lenses 38. It is further contemplated that the depressions 36 can have shapes other than circular, such as oval, rectangular, triangular, or irregular.

The configuration of the lens array, including the spacing between the circular depressions 36, corresponds to the configuration and spacing of the image sensor array in the intermediate membrane 14 below. Narrow grooves 40 that are preferably shallower than the circular depressions 36 are also formed in the bottom surface of the outer membrane 16 during the lithography process. The grooves 40 intersect, and extend away from, the circular depressions 36 to at least one fluid inlet 42 that is preferably located intermediate the lens array and an edge of the membrane 16, although the particular location of the fluid inlet 42 is not critical. The configuration of the grooves 40 and the fluid inlet 42 will be described in greater detail below.

Figure 3:
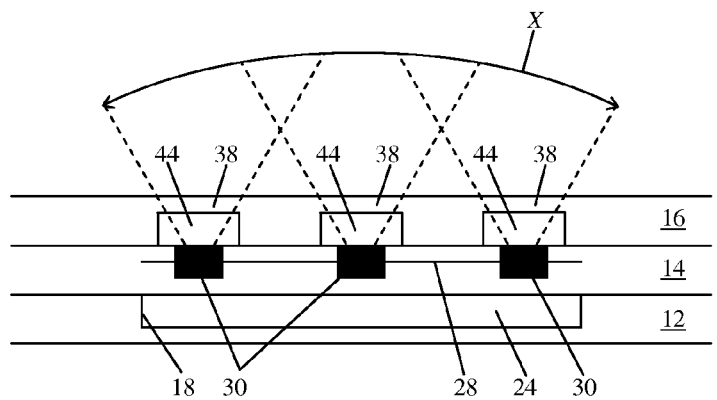
FIG. 3 is a view in section illustrating the preferred embodiment of the present invention shown in FIG. 1 with the eye in a planar configuration.

The outer membrane 16 is bonded to the top surface of the intermediate membrane 14 in a flatly abutting relationship therewith using a conventional covalent bonding process. The lens array in the outer membrane 16 is aligned with the image sensor array in the intermediate membrane 14, with each lens 38 positioned directly above an image sensor 30 as shown in FIG. 3. With the bottom surface of the outer membrane 16 bonded to the flat top surface of the intermediate membrane 14 thusly, the circular depressions 36 in the outer membrane 16 (described above) form substantially enclosed, circular fluid chambers 44, hereinafter referred to as "focus chambers 44," between the lenses 38 and the image sensors 30. Similarly, the grooves 40 in the outer membrane 16 form enclosed, microfluidic channels 46 (see FIG. 1) between the membranes 14 and 16 that are in fluid communication with the focus chambers 44 to which they extend.

The focus chambers 44 and the microfluidic channels 46 contain a refractive fluid medium that is kept under pressure by a series of computer controlled, microfluidic pumps (not shown) that are operatively connected to the microfluidic channels 46 at the fluid inlet 42. The refractive medium is preferably mineral oil (refractive index n=1.4), although it is contemplated that any suitable fluid medium with a refractive index greater than 1.00 can alternatively be used. The purpose and operation of the circular focus 44 chambers and the pressurized refractive medium will be described in greater detail below.

During normal operation of the eye 10 (described in greater detail below), incoming light passes through each of the lenses 38 in the lens array, as well as through the refractive fluid media contained in the focus chambers 44 between the lenses 38 and the image sensors 30. The light is then received by the image sensors 30, where it is converted to an electrical output signal and transmitted to a processing unit in the manner described above.

The mechanical operation of the artificial compound eye 10 includes two general functions: 1) manipulation of the eye's total field of view; and 2) manipulation of the focal length of each individual lens 38. These functions and their respective applications will now be described in detail.

Manipulation of Field of View (FOV)

Referring to FIG. 3, the artificial compound eye 10 is shown in an unpressurized, planar configuration, wherein the fluid in the circular field chamber 24 is not pressurized, or is only nominally pressurized, by the computer-controlled, microfluidic pump (described above) that is connected thereto. In this configuration, the portion of the intermediate membrane 14 that forms the ceiling of the field chamber 24 and that houses the image sensor array is substantially flat. The image sensors 30 are therefore aligned in a substantially parallel configuration with each sensor 30 pointing directly forward (i.e. perpendicular to the plane of the substrate membrane 12, or directly up in FIG. 3). The FOV of the compound eye 10 in this configuration is indicated at X, and extends from the leftmost boundary of the FOV of the leftmost image sensor 30 to the rightmost boundary of the FOV of the rightmost image sensor 30.

Figure 4:
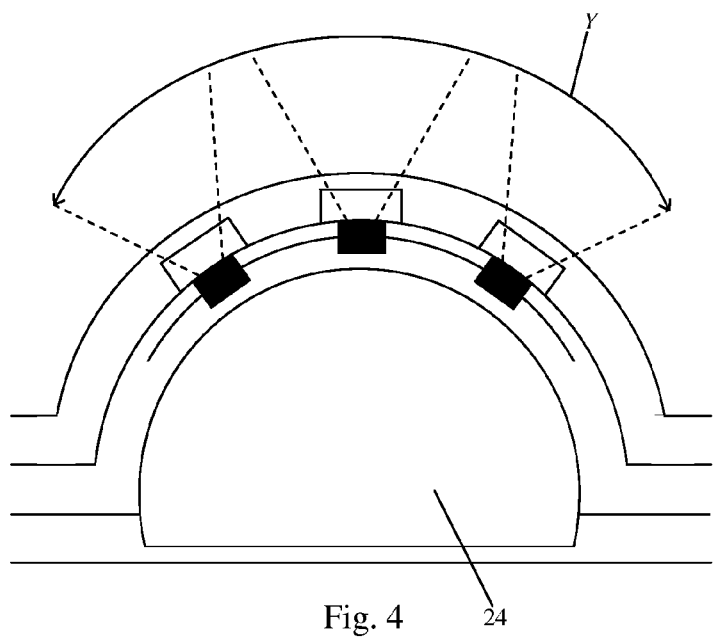
FIG. 4 is a view in section illustrating the preferred embodiment of the present invention shown in FIG. 1 with the eye in a domed configuration.
Figure 5:
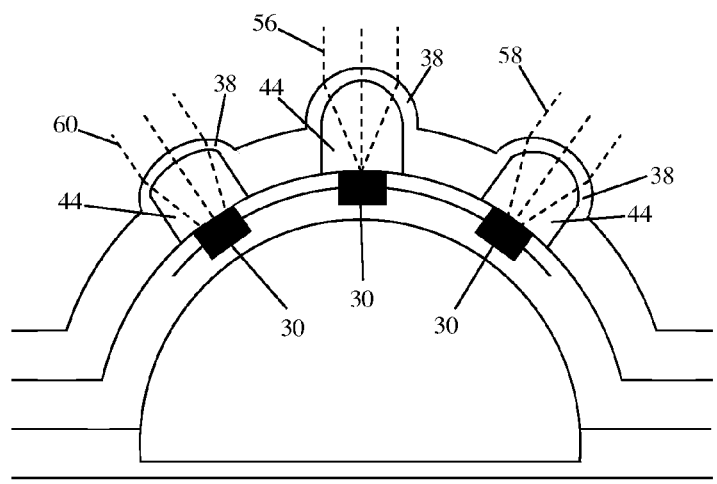
FIG. 5 is a view in section illustrating the preferred embodiment of the present invention shown in FIG. 1 with the eye in a domed configuration and several lenses of the eye in various domed configurations.

Referring to FIGS. 4 and 5, the artificial compound eye 10 is shown in a convex, pressurized configuration, wherein, relative to the planar configuration of the eye 10 shown in FIG. 3, a quantity of fluid has been introduced into the field chamber 24 by its corresponding microfludic pump. The introduction of fluid into the field chamber 24 causes the flexible ceiling of the chamber 24 to expand outwardly under pressure, causing the intermediate membrane 14 and the outer membrane 16 to form substantially hemispherical, adjoining domes. In this configuration, the flexible circuit 28 of the image sensor array is also flexed outwardly into a convex shape, resulting in the image sensors 30 pointing in directions that are angularly offset relative to one another, with the degree of offset of each sensor 30 relative to perpendicular (i.e. perpendicular to the plane of the substrate membrane 12) increasing as the distance of the sensor 30 from the apex of the domed eye 10 increases. The FOV of the compound eye 10 in this configuration is indicated at Y, and extends from the leftmost boundary of the FOV of the leftmost image sensor 30 to the rightmost boundary of the FOV of the rightmost image sensor 30.

Figure 12:
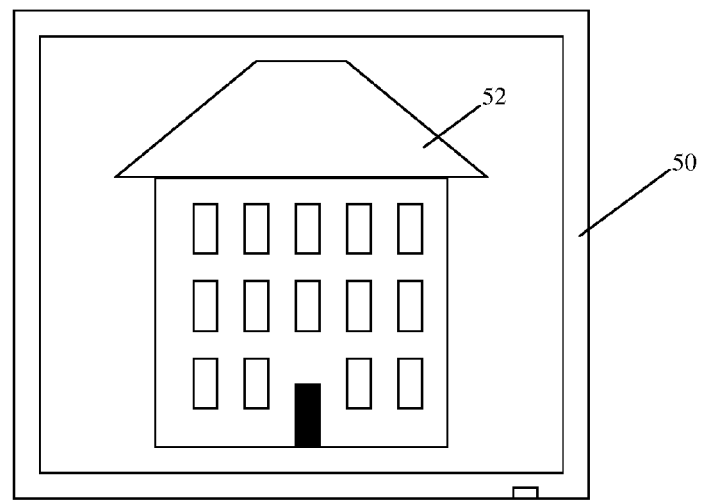
FIG. 12 is a schematic view illustrating a first display image facilitated by the eye.
Figure 13:
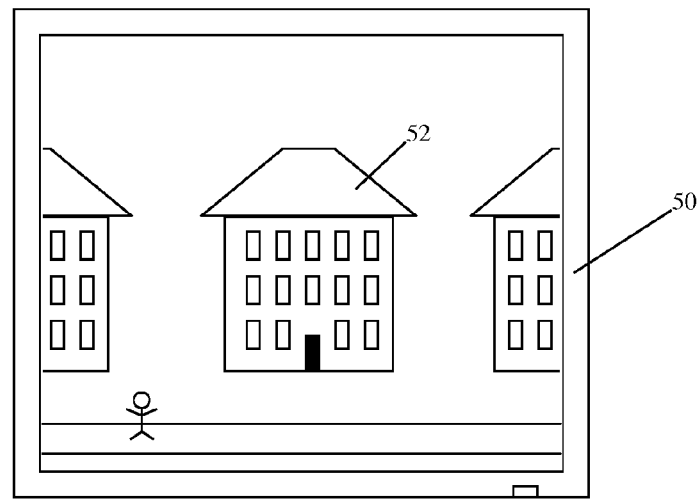
FIG. 13 is a schematic view illustrating a second display image facilitated by the eye.

Looking at FIGS. 3 and 4, it is readily apparent that the FOV Y of the convex, domed configuration of the compound eye 10 is significantly greater than the FOV X of the planar configuration of the eye 10. This increase is attributable to the outward deflection of the image sensors 30 relative to their orientation in the planar configuration of the eye 10. A user can thus manipulate the FOV of the artificial compound eye 10 by varying the fluid pressure that is applied to the field chamber 24 by the computer-controlled, microfluidic pump, such as by operating an input means (e.g. buttons, joystick, alphanumeric input, etc) that is provided for accepting such user input. For example, a user may decrease the fluid pressure applied by the microfluidic pump and minimize the FOV of the eye 10 in order to limit his or her view to a particular object or structure captured by the eye 10 while omitting distracting surrounding objects and structures. FIG. 12 illustrates such a scenario, wherein the user has decreased the convexity (FOV) of the eye 10 in order to limit his view, as presented on the computer monitor 50, to the building 52. Alternatively, the user may wish to increase the fluid pressure applied by the microfluidic pump and maximize the FOV of the eye 10 in order to view an object or structure in the context of its surrounding environment. For example, referring to FIG. 13, the user has increased the convexity of the eye 10 relative to the scenario illustrated in FIG. 12 to expand the FOV of the eye 10 in order to view the building 52 as well its surrounding environment. It is contemplated that the manipulation of the FOV of the eye 10 can be partially or fully automated. For example, the operation of the microfluidic pump can be coupled to a motion detection means wherein the microfluidic pump will expand the FOV of the eye 10 (i.e. if further expansion is possible) if the motion detection means detects motion outside of the eye's then-current FOV.

Manipulation of Focal Length (FL)

Referring again to FIGS. 3 and 4, each of the lenses 38 of the artificial compound eye 10 is shown in a planar configuration, wherein the fluid in each of the circular focus chambers 44 is not pressurized, or is only nominally pressurized, by the computer-controlled, microfluidic pump (described above) that is connected thereto. In this configuration, the lenses 38 are substantially flat (as in the planar configuration of the eye 10 shown in FIG. 3) or are subtly curved (as in the domed configuration of the eye shown in FIG. 4). When the lenses 38 are substantially flat, the focal length of each lens 38 is infinite or near infinite. That is, initially colineated rays of light that enter each lens 38 are not converged or focused by the lens 38. The rays of light simply continue through the lens 38 in a generally straight, unaltered path, through the refractive medium and onto the underlying image sensor 30.

Referring to FIG. 5, the lenses 38 are shown in a variety of convex, pressurized configurations wherein, relative to the substantially planar configuration of the lenses 38 shown in FIGS. 3 and 4, a quantity of refractive fluid has been introduced into each of the focus chambers 44 by its respective, microfludic pump, or by a valve (described below). As with the field chamber 24 described above, the introduction of refractive fluid into the focus chambers 44 causes the lenses 38 to expand outwardly under pressure. The convexity of each lens 38 increases as the fluid pressure inside each lens's respective focus chamber 44 is increased. For example, with regard to the lenses 38 shown in FIG. 5, the leftmost lens 38 is subject to the least amount of fluid pressure and therefore exhibits the least convexity. The rightmost lens 38 is subject to a greater amount of fluid pressure than the leftmost lens 38 and therefore exhibits greater convexity. The middle lens 38 is subject to the greatest amount of fluid pressure and therefore exhibits the greatest convexity. As will be appreciated by those skilled in the art, an increase in the convexity of a lens 38 results in a decrease of the lens's focal length. That is, as the convexity of a lens 38 increases, the distance over which initially colineated rays of light entering the lens 38 are converged decreases. This is illustrated in FIG. 5, wherein rays of light 56 entering the most convex, middle lens 38 are completely converged when they reach the image sensor 30. By contrast, the rays of light 58 entering the less convex, rightmost lens 38 are less converged when they reach the image sensor 30, and the rays of light 60 entering the least convex, leftmost lens 38 are less converged still when they reach the image sensor 30.

This relationship between fluid pressure and focal length is further illustrated in FIG. 14, wherein a ray trace method has been employed to show the degree of convergence of a laser beam with a wavelength of 540 nm as it passes through a lens 38 of the eye 10. It can be seen that as the fluid pressure of the refractive medium in the lens's focus chamber 44 is increased from zero to a limited value, the focal length can be tuned from +∞ to less than 1 mm. This relationship is further illustrated in the graph shown in FIG. 15. It is contemplated that the relationship between the focal length and the fluid pressure can vary with the dimensions of the lens 38, the focus chamber 44, and the microfluidic channel 46, as well as with the particular the refractive medium used.

A user can thus independently manipulate the focal length of each of the lenses 38 of the eye 10 by varying the fluid pressure that is applied to a lens's focus chamber 44 by its respective, computer-controlled, microfluidic pump, such as by operating an input means (e.g. buttons, joystick, alphanumeric input, etc) that is provided for accepting such user input. Each lens 38 is connected to its respective microfluidic pump through the microfluidic channel 46. Two typical arrangements of microfluidic channels for two alternative lens configurations are shown in FIGS. 6 and 7. Alternatively, it is contemplated that all of the focus chambers 44 can be connected to a single microfluidic pump, with the pressure in each focus chamber 44 regulated by a valve that is driven by piezoelectric method. Two typical arrangements of such valves are shown in FIGS. 8 and 9 (the valves are indicated by pairs of opposing arrows). It is contemplated that other suitable arrangements of microfluidic channels and valves can be implemented without departing from the present invention. It is also contemplated that the valves can alternatively be driven by any other physical or chemical actuation methods, such as through the use of using electroactive polymers and bi-morph structures.

In the preferred embodiment of the invention, the microfluidic pumps of the eye 10 are controlled automatically by digital processing means that employ well known auto-focus techniques. Such processing means can be integrated into the structure of the eye 10 or can be located in close proximity to the eye 10, or can be located remotely and operatively connected to the eye 10 through wired or wireless communication means. The ability to independently tune the focal length of each individual lens 38 allows the compound eye 10 to simultaneously focus on a plurality of objects at various distances from the eye 10 without moving the eye 10 nearer to or further from the objects. This eliminates the need for cumbersome mechanical structures that are typically employed in traditional camera lenses for enabling physical movement of a lens.

Advantages of Variable FOV

The above-described structure and operation of the eye 10 provide distinct advantages over the capability of traditional camera lenses. A first such advantage is that the FOV of the eye 10 is not coupled to any particular focal length. That is, in order to obtain a wide FOV with a conventional, fixed-configuration lens, the lens must be significantly convex with a relatively short focal length. The working distance of the lens is therefore restricted to relatively short distances. By contrast, the FOV of the eye 10 is realized by the arrangement and orientation of the lenses 38 on the variably-domed, intermediate membrane 14 of the eye 10, and is not substantially affected by variations in the focal lengths of the individual lenses 38. The eye 10 can therefore provide a wide FOV while one or more of the eye's lenses 38 are tuned to have long focal lengths and long working distances.

A second advantage of the eye 10, and a corollary to the first advantage described above, is an absence of image distortion when the eye 10 is in a wide FOV configuration. That is, traditional wide-angle and fisheye lenses are highly convex and therefore significantly bend incoming light. Light that enters such a lens at points further from the lens's apex is bent to a greater degree than light that enters the lens at points nearer the lens's apex. Images produced by such lenses therefore exhibit distortion in the form of severe bowing near the periphery of the image. By contrast, the curvature and corresponding FOV of the eye 10 bear no relationship to the curvature of each of the eyes lenses 38. Each individual lens 38 is only responsible for capturing the viewable field ahead of it. Incoming light therefore does not have to be bent to an extreme degree in order for the eye 10 to produce wide angle images, thereby facilitating high quality images that do not exhibit distortion.

Three Dimensional Imaging

In addition to the benefits described above, the multiple, independently-tunable lenses of the eye 10 facilitate real-time, 3D imaging of objects with accurate depth information. Referring to FIG. 16, this is accomplished by bringing a plurality of the eye's lenses 38 to focus on different areas of an object's surface by simultaneously tuning the fluid pressure in a plurality of the eye's focus chambers 44. After each of the lenses 38 has been brought to focus on a designated area of the object, the measured amount of fluid pressure that is applied to each lens 38 is used to determine the distance between the lenses 38 and the captured areas of the object. The relationship between working distance and fluid pressure is an inverse one, with the fluid pressure in a lens's focus chamber 44 increasing as the distance between the lens and an object that is brought into focus decreases. The distances between the lenses 38 and the captured areas of the object are thereby computed in real-time by the CPU 32 to which the eye 10 is connected (as described above). The calculated distances are then used to construct a digital, 3D representation of the captured object which is then presented to a viewer as shown in FIG. 16.

Applications

It is contemplated that the advanced artificial compound eye 10 of the present invention can be applied in many areas where a broad field of view with high resolution is critical. For example, in the biomedical field, this device can be integrated into medical devices such as endoscopes to examine the 3D shape and morphology of target tissues or organs inside human bodies, such as for facilitating diagnoses and surgical processes. It is further contemplated that the inventive eye 10 can be employed in military applications, wherein the eye 10 can be used as a surveillance instrument for wide-field monitoring. Additionally, when used in conjunction with image reconstruction technologies, the motion of target objects can be captured by analyzing image series acquired by the individual lenses 38 of the eye 10. Such motion capture can be utilized in situations where motion detection plays an important role, such as in determining the real-time positions of missiles or fighter planes. In the consumer products industry, it is contemplated that the inventive eye 10 can be integrated into digital cameras and cellular telephones to enhance the functionality and size/weight characteristics of current products.

This detailed description in connection with the drawings is intended principally as a description of the presently preferred embodiments of the invention, and is not intended to represent the only form in which the present invention may be constructed or utilized. The description sets forth the designs, functions, means, and methods of implementing the invention in connection with the illustrated embodiments. It is to be understood, however, that the same or equivalent functions and features may be accomplished by different embodiments that are also intended to be encompassed within the spirit and scope of the invention and that various modifications may be adopted without departing from the invention or scope of the following claims.

The invention claimed is:

1. An artificial compound eye comprising:
   a) a substantially planar first layer of material;

b) an image sensor array mounted to the first layer;
c) a second layer of material having a void and fluid in the void, the second layer bonded to a first side of the first layer, thereby forming the void between the first layer and the second layer;
d) a field pump in fluid communication with the void and a source of fluid;
e) a third layer of material bonded to a second side of the first layer opposite the first side; and
f) a plurality of lenses on the third layer and distributed in a predetermined pattern;
wherein each of the lenses has a corresponding chamber formed between the third layer and the first layer containing fluid in fluid communication with at least one lens pump;
wherein each of the lenses is formed by at least a portion of the third layer of material; and
wherein each image sensor in the array is positioned adjacent a corresponding one of the lenses for receiving light that passes through the corresponding lens and fluid in the corresponding chamber.

2. The artificial compound eye in accordance with claim 1, further comprising a central processing unit to which image data captured by each of the image sensors is communicated.

3. The artificial compound eye in accordance with claim 2, further comprising wireless communications means through which the image data is transmitted.

4. The artificial compound eye in accordance with claim 2, wherein the central processing unit further comprises means for utilizing the image data from the image sensors to form a single, contiguous image that is presented on a display.

5. The artificial compound eye in accordance with claim 1, wherein the first layer of material is formed of an elastic membrane.

6. The artificial compound eye in accordance with claim 1, wherein the first layer of material is formed of a rigid membrane.

7. The artificial compound eye in accordance with claim 1, further comprising a microfluidic channel extending from the void to the field pump for allowing fluid to be controllably supplied to and removed from the void to facilitate deformation of at least the first layer.

8. The artificial compound eye in accordance with claim 7, wherein the field pump is operatively connected to a central processing unit that controls the field pump.

9. The artificial compound eye in accordance with claim 7, wherein the fluid in the void is a liquid.

10. The artificial compound eye in accordance with claim 7, wherein the fluid in the void is a gas.

11. The artificial compound eye in accordance with claim 1, further comprising a microfluidic channel extending from each of the lens chambers to said at least one lens pump for allowing fluid to be controllably supplied to and removed from each lens chamber to facilitate deformation of at least a portion of the third layer.

12. The artificial compound eye in accordance with claim 11, wherein said at least one lens pump is operatively connected to a central processing unit that controls said at least one lens pump.

13. The artificial compound eye in accordance with claim 11, wherein said at least one lens pump comprises a single lens pump and wherein each microfluidic channel is operatively connected to a corresponding valve for allowing fluid to be controllably supplied to and removed from each lens chamber to facilitate deformation of at least a portion of the third layer.

14. The artificial compound eye in accordance with claim 13, wherein each of the valves is operatively connected to a central processing unit that controls the valves.

15. The artificial compound eye in accordance with claim 11, wherein the fluid in the lens chambers is a liquid having a refractive index greater than 1.00.

16. The artificial compound eye in accordance with claim 7, wherein at least one of the first layer of material, the second layer of material, and the third layer of material is formed of an elastic membrane.

17. An artificial compound eye comprising:
a) a substantially planar first layer of material;
b) a second layer of material bonded to a first side of the first layer and forming a void therebetween, wherein the void is filled with fluid;
c) a field pump in fluid communication with the void and a source of fluid;
d) a third layer of material bonded to a second side of the first layer opposite the first side;
e) a plurality of lenses formed in the third layer of material and distributed in a predetermined pattern;
f) an image sensor array mounted to the first layer, each image sensor being positioned adjacent a corresponding one of the lenses for receiving light that passes through the corresponding lens and wherein the lenses have corresponding chambers in fluid communication with at least one lens pump; and
g) a microfluidic channel extending from the void to the field pump for allowing fluid to be controllably supplied to and removed from the void to facilitate deformation of at least the first layer.

18. The artificial compound eye in accordance with claim 17, further comprising a central processing unit to which image data captured by each of the image sensors is communicated.

19. The artificial compound eye in accordance with claim 18, further comprising wireless communications means through which the image data is transmitted.

20. The artificial compound eye in accordance with claim 18, wherein the central processing unit further comprises means for utilizing the image data from the image sensors to form a single, contiguous image that is presented on a display.

21. The artificial compound eye in accordance with claim 17, wherein the field pump is operatively connected to a central processing unit that controls the field pump.

22. The artificial compound eye in accordance with claim 17, wherein the fluid in the void is a liquid.

23. The artificial compound eye in accordance with claim 17, wherein the fluid in the void is a gas.

24. The artificial compound eye in accordance with claim 17, wherein at least one of the first layer of material, the second layer of material, and the third layer of material is formed of an elastic membrane.

25. An artificial compound eye comprising:
a) a substantially planar first layer of material;
b) a second layer of material bonded to a first side of the first layer and forming a void therebetween, wherein the void is filled with fluid;
c) a field pump in fluid communication with the void and a source of fluid;
d) a third layer of material bonded to a second side of the first layer opposite the first side.
e) a plurality of lenses formed in the third layer of material and distributed in a predetermined pattern, wherein each of the lenses has a corresponding chamber containing fluid in fluid communication with at least one lens pump;

f) an image sensor array mounted to the first layer, each image sensor being positioned adjacent a corresponding one of the lenses for receiving light that passes through the corresponding lens and fluid in the corresponding chamber; and g) a microfluidic channel extending from each of the lens chambers to said at least one lens pump for allowing fluid to be controllably supplied to and removed from each lens chamber to facilitate deformation of at least a portion of the third layer.

26. The artificial compound eye in accordance with claim 25, wherein said at least one lens pump is operatively connected to a central processing unit that controls the lens pumps.

27. The artificial compound eye in accordance with claim 25, wherein said at least one lens pump comprises a single lens pump and wherein each microfluidic channel is operatively connected to a corresponding valve for allowing fluid to be controllably supplied to and removed from each lens chamber to facilitate deformation of each lens.

28. The artificial compound eye in accordance with claim 27, wherein each of the valves is operatively connected to a central processing unit that controls the valves.

29. The artificial compound eye in accordance with claim 25, wherein the fluid in the lens chambers is a liquid having a refractive index greater than 1.00.

* * * * *

UNITED STATES PATENT AND TRADEMARK OFFICE
CERTIFICATE OF CORRECTION

PATENT NO.        : 8,964,019 B2                                        Page 1 of 1
APPLICATION NO.   : 13/336075
DATED             : February 24, 2015
INVENTOR(S)       : Yi Zhao et al.

It is certified that error appears in the above-identified patent and that said Letters Patent is hereby corrected as shown below:

In The Claims

Col. 12, Line 8, delete "7" and add --1--

Signed and Sealed this
Nineteenth Day of May, 2015

Michelle K. Lee
*Director of the United States Patent and Trademark Office*